United States Patent
Cho et al.

(10) Patent No.: US 9,206,147 B2
(45) Date of Patent: Dec. 8, 2015

(54) METHOD FOR PRODUCING 5-HYDROXYMETHYL-2-FURFURAL OR ALKYL ETHER DERIVATIVES THEREOF USING AN ION EXCHANGE RESIN IN THE PRESENCE OF AN ORGANIC SOLVENT

(75) Inventors: Jin Ku Cho, Yongin-si (KR); Sang Yong Kim, Cheonan-si (KR); Jae Hoon Cho, Gwangju-si (KR); Bo Ra Kim, Daejeon-si (KR); Paul Joo, Montreal (CA)

(73) Assignee: KOREA INSTITUTE OF INDUSTRIAL TECHNOLOGY, Cheonan-si, Chungcheongam-do (KR)

( * ) Notice: Subject to any disclaimer, the term of this patent is extended or adjusted under 35 U.S.C. 154(b) by 0 days.

(21) Appl. No.: 14/348,566

(22) PCT Filed: Jul. 9, 2012

(86) PCT No.: PCT/KR2012/005408
§ 371 (c)(1),
(2), (4) Date: Mar. 28, 2014

(87) PCT Pub. No.: WO2013/047984
PCT Pub. Date: Apr. 4, 2013

(65) Prior Publication Data
US 2014/0235881 A1 Aug. 21, 2014

(30) Foreign Application Priority Data
Sep. 29, 2011 (KR) .......................... 10-2011-0099424

(51) Int. Cl.
C07D 407/00 (2006.01)
C07D 307/50 (2006.01)
C07D 307/48 (2006.01)
C07D 307/46 (2006.01)

(52) U.S. Cl.
CPC ............ *C07D 307/50* (2013.01); *C07D 307/46* (2013.01); *C07D 307/48* (2013.01)

(58) Field of Classification Search
CPC ............................ C07D 307/48; C07D 307/50
USPC .......................................................... 549/488
See application file for complete search history.

(56) References Cited

FOREIGN PATENT DOCUMENTS

| JP | 55-053280 A | 4/1980 |
| KR | 10-2009-0024664 A | 3/2009 |
| KR | 10-2011-0016638 A | 2/2011 |

OTHER PUBLICATIONS

PCT International Search Report for PCT/KR2012/005408.

*Primary Examiner* — Andrew D Kosar
*Assistant Examiner* — Raymond Covington
(74) *Attorney, Agent, or Firm* — Lucas & Mercanti, LLP (57) ABSTRACT

The present invention relates to a method for producing a furan-based compound using an ion exchange resin in the presence of an organic solvent. In the method for producing a furan-based compound according to the present invention, a furan-based compound is made from an aldose-type hexose compound in the presence of an organic solvent by using an anion exchange resin and a cation exchange resin. Thus, the aldose-type hexose compound obtained from biomass by simultaneously or consecutively using the anion/cation exchange resins as catalysts can be made into 5-hydroxymethyl-2-furfural (HMF) or alkyl ether derivatives thereof such as 5-alkoxymethyl-2-furfural (AMF) without using an expensive reagent. Also, since the selection of an organic solvent is not limitative and a heterogeneous catalyst can be used, separation and purification is easy and chemically stable AMF can be directly obtained. Further, the conversion efficiency of the aldose-type hexose compound is excellent, and the hexose compound can be used at a high concentration.

17 Claims, 6 Drawing Sheets

FIG. 6

METHOD FOR PRODUCING 5-HYDROXYMETHYL-2-FURFURAL OR ALKYL ETHER DERIVATIVES THEREOF USING AN ION EXCHANGE RESIN IN THE PRESENCE OF AN ORGANIC SOLVENT

CROSS-REFERENCE TO RELATED APPLICATIONS

This application is a 371 of PCT/KR2012/005408, filed Jul. 9, 2012, which claims the benefit of Korean Patent Application No. 10-2011-0099424, filed Sep. 9, 2011, the contents of each of which are incorporated herein by reference.

TECHNICAL FIELD

The present invention relates to a method of producing a furan-based compound using an ion exchange resin in the presence of an organic solvent, and more particularly, to a method of producing 5-hydroxymethyl-2-furfural (HMF) or 5-alkoxymethyl-2-furfural (AMF) as an ether derivative thereof from a biomass-derived aldose-type hexose compound by simultaneously or consecutively using an anion exchange resin and a cation exchange resin.

BACKGROUND ART

With a continuous reduction in limited oil resources and also a drastic increase in oil demand due to growth of emerging developing countries, an imbalance of supply and demand in the market is caused, resulting in high oil prices. Furthermore, irreversible greenhouse gas generated by indiscriminate use of oil may incur serious environmental problems such as global warming.

Countries around the world already have made many efforts to replace oil resources through biomass which is recyclable and reusable, and biofuels such as bioethanol, biodiesel, etc., and bioplastic monomers such as lactic acid, propanediol, etc. are industrially produced and thus replace transportation fuels or petrochemical materials.

As part of these efforts, materials which are recently spotlighted are exemplified by biomass-derived furan-based compounds, that is, 5-hydroxymethyl-2-furfural (HMF) and 5-alkoxymethyl-2-furfural (AMF) as an alkyl ether derivative thereof.

HMF and AMF may be converted into 2,5-furan dicarboxylic acid (FDCA) via oxidation, and FDCA is known to be an alternative to terephthalic acid (TPA) which is a monomer of PET (Poly(ethylene terephthalate)) widely useful in vessels for beverages and food, etc. PET is obtained from ethylene glycol (EG) and TPA monomers through polycondensation. Currently, in order to prepare biomass-based PET, the EG monomer is being industrially produced from bioethanol-based bioethylene, but TPA is not yet obtained from any biomass-based material.

Also, AMF is known to be a next-generation biofuel, and has an energy density equal to or more than that of gasoline, and has no problems related to extended storage and corrosion due to low hygroscopicity, unlike bioethanol. Moreover, in the case of bioethnaol produced through an enzyme conversion process, it essentially emits 2 equiv. carbon dioxide from 1 equiv. hexose in the process ($C_6H_{10}O_6 \rightarrow 2CH_3CH_2OH\ 2CO_2\uparrow$), whereas AMF may be produced using a complete carbon-neutral process without carbon loss.

5-hydroxymethyl-2-furfural (HMF) and 5-alkoxymethyl-2-furfural (AMF) may be obtained from polysaccharide materials composed of hexoses such as sugars, starch, cellulose, agar (red algae) among carbohydrate components present in biomass. Specifically, polysaccharide materials composed of hexoses such as sugars, starch, cellulose, agar (red algae) are converted into monosaccharide materials such as fructose, glucose and galactose through saccharification based on hydrolysis, and 3 equiv. water molecules are removed from the monosaccharide materials thus converted under dehydration conditions, thus producing HMF or AMF.

The hexose compound of the monosaccharide such as fructose, glucose or galactose includes two kinds of structural isomers, for examples, ketose and aldose. Ketose and aldose may be sorted depending on the position of the carbonyl group, wherein ketose is a ketone compound having a carbonyl group at C2, and aldose is an aldehyde compound having a carbonyl group at C1.

Also, the hexose compound exists while forming an equilibrium relation between a linear structure and a ring structure depending on pH conditions. As such, ketose forms a five-membered ring structure, and aldose forms a six-membered ring structure.

Thus, when obtaining HMF and AMF as furan-based compounds having a five-membered ring structure from the hexose compound of the monosaccharide, ketose is known to be much easier in terms of conversion, compared to aldose. Hence, to produce HMF or AMF, fructose which is ketose is generally used as a starting material.

However, most of hexose compounds existing in nature are aldose such as glucose or galactose, and ketose such as fructose is limitedly present in sugars, milk, etc. Methods of converting glucose into fructose through enzyme conversion are known, and such glucose is mass produced in the form of high-concentration fructose and is thus utilized in food additives, etc. However, compared to direct use of glucose, additional process costs are required and about 50% glucose is present even in high-concentration fructose.

Thus, research into directly obtaining HMF and AMF from aldose such as glucose that is the hexose compound very abundant in nature is ongoing currently.

With the goal of directly producing HMF and AMF from aldose, isomerization conditions for converting aldose into ketose are required. The most typical method known to date is the use of a Cr(II) or Cr(III) catalyst in the presence of an imidazolium type ionic liquid solvent (Science 2007; 316; 1597-1600). However, this method is undesirable in terms of profitability upon industrial mass production because the ionic liquid solvent used is expensive.

Another method is reported to be a method of maximizing conversion efficiency through real-time extraction of a produced furan-based compound using a biphasic system (Science, 2006; 312; 1933-1937). However, because this method provides no additional isomerization conditions, it is mainly effectively applied to fructose which is ketose rather than aldose, and in order to maintain the biphasic system during the reaction, the selection of the solvent is limited, and the use of a heterogeneous catalyst is difficult. Also, the furan-based product resulting from both the methods as above is limited to HMF. Furthermore, HMF, which is unstable compared to AMF, is partially decomposed in the course of recovery from the reaction mixture, which is undesirable.

International Patent Application No. WO 2007/104514 discloses a method of synthesizing AMF, comprising converting a hexose compound using a solid acid catalyst in the presence of an alcohol solvent. However, because this method provides no additional isomerization conditions like the biphasic system conversion method, it is mainly effectively applied to fructose which is ketose. Also, the concentration of the hexose compound which is the substrate under reaction conditions is as low as about 1% (wt/V), undesirably increasing production and recovery process costs.

DISCLOSURE

Technical Problem

Accordingly, the present invention is intended to provide a method of producing 5-hydroxymethyl-2-furfural (HMF) or 5-alkoxymethyl-2-furfural (AMF) as an ether derivative thereof from an aldose-type hexose compound, wherein an anion exchange resin and a cation exchange resin may be simultaneously or consecutively used in the presence of not an aqueous solution but an organic solvent, thereby obviating the need for expensive reagents, facilitating separation and purification, and making it possible to directly produce chemically stable AMF.

Technical Solution

In order to accomplish the above object, the present invention provides a method of producing a furan-based compound, comprising producing a furan-based compound from an aldose-type hexose compound using an anion exchange resin and a cation exchange resin in the presence of an organic solvent.

This method may comprise subjecting the aldose-type hexose compound to isomerization using the anion exchange resin to give a ketose-type hexose compound (step 1); and dehydrating the ketose-type hexose compound using the cation exchange resin to give the furan-based compound (step 2).

The anion exchange resin and the cation exchange resin may be used simultaneously or consecutively.

The aldose-type hexose compound may be aldose-type glucose; aldose-type galactose; or a saccharide compound including aldose-type glucose or aldose-type galactose.

The saccharide compound including aldose-type glucose or aldose-type galactose may be amylose, cellulose or agarose.

The furan-based compound may be 5-hydroxymethyl-2-furfural (HMF) or 5-alkoxymethyl-2-furfural (AMF).

The alkoxy group of 5-alkoxymethyl-2-furfural (AMF) may be a C1~C5 alkoxy group.

The anion exchange resin may be a basic anion exchange resin as a polystyrene-based bead resin, which has a quaternary ammonium or tertiary amine functional group at a terminal thereof and in which a central ion is substituted with bicarbonate or aluminate and thus pH around the exchange resin falls in the range of 12~13.

The cation exchange resin may be an acidic cation exchange resin as a polystyrene-based bead resin, which has a sulfonic acid functional group at a terminal thereof and in which a central ion is substituted with a proton and thus pKa is 1~2.

The organic solvent may be an aprotic polar solvent.

The aprotic polar solvent may be any one selected from among dioxane, tetrahydrofuran (THF), acetone, dimethyl sulfoxide (DMSO), dimethylformamide (DMF) and 1-methyl-2-pyrrolidone (NMP).

The organic solvent may be a protic polar solvent.

The protic polar solvent may be an alcohol solvent.

The protic polar solvent may be any one selected from among ethanol, n-butanol and isopropanol.

The aldose-type hexose compound may have a concentration of 1~30% (wt/V) in a mixed solution with the organic solvent.

The anion exchange resin may be used in an amount of 50~300 parts by weight based on 100 parts by weight of the aldose-type hexose compound.

Furthermore, producing the furan-based compound may be performed at a reaction temperature of 50~200° C.

Advantageous Effects

In a production method according to the present invention, anion/cation exchange resins are simultaneously or consecutively used as catalysts, and thereby an aldose-type hexose compound obtained from biomass can be made into 5-hydroxymethyl-2-furfural (HMF) or its alkyl ether derivative, that is, 5-alkoxymethyl-2-furfural (AMF), without the use of expensive reagents.

Also, the selection of an organic solvent is not limited, and the use of a heterogeneous catalyst is possible, thus facilitating separation and purification and directly producing chemically stable AMF. Furthermore, the conversion efficiency of the aldose-type hexose compound is high, and the hexose compound can be used at as high a concentration as at least 10-fold.

BEST MODE

Hereinafter, a detailed description will be given of a method of producing 5-hydroxymethyl-2-furfural or alkyl ether derivatives thereof using an ion exchange resin according to the present invention.

As such, 5-hydroxymethyl-2-furfural (HMF) or 5-alkoxymethyl-2-furfural (AMF) as an alkyl ether derivative thereof is represented by Chemical Formula 1 below.

[Chemical Formula 1]

R = H : 5-hydroxymethyl-2-furfural (HMF)
R = Alkyl : 5-alkoxymethyl-2-furfural (AMF)

In the method of producing the furan-based compound according to the present invention, an aldose-type hexose compound is made into a furan-based compound using an anion exchange resin and a cation exchange resin in the presence of an organic solvent.

Specifically, the method of producing 5-hydroxymethyl-2-furfural and derivatives thereof according to the present invention includes subjecting an aldose-type hexose compound to isomerization using an anion exchange resin to give a ketose-type hexose compound (step 1); and dehydrating the ketose-type hexose compound using a cation exchange resin to give a furan-based compound (step 2).

Step 1 is converting the aldose-type hexose compound into the ketose-type hexose compound through isomerization using the anion exchange resin.

The hexose compound includes two kinds of structural isomers comprising ketose and aldose.

As used herein, the term "aldose-type hexose compound" refers to a monosaccharide with six carbon atoms as aldose which is a monosaccharide containing one aldehyde per mole. As used herein, the term "ketose-type hexose compound" refers to a monosaccharide with six carbon atoms as ketose which is a monosaccharide containing one ketone per mole.

As represented by Chemical Formula 2 below, ketose and aldose are sorted depending on the position of the carbonyl group, wherein ketose is a ketone compound having a carbonyl group at C2, and aldose is an aldehyde compound having a carbonyl group at C1.

[Chemical Formula 2]

Aldose
(Glucose)

Ketose
(Fructose)

Also, the hexose compound exists while forming an equilibrium relation between a linear structure and a ring structure depending on pH conditions. As such, ketose forms a five-membered ring structure, and aldose forms a six-membered ring structure, as represented by [Chemical Formula 2].

Thus, when obtaining HMF and AMF which are furan-based compounds having a five-membered ring structure from the hexose compound of the monosaccharide, ketose is much more easily converted compared to aldose. Accordingly to produce HMF or AMF, the use of ketose as a starting material is preferable. To this end, aldose which constitutes most of the hexose compounds existing in nature may be converted into ketose at a high yield by the reaction of step 1.

In the reaction of step 1, the aldose-type hexose compound may be aldose-type glucose, aldose-type galactose or a saccharide compound including aldose-type glucose or aldose-type galactose. Also, the saccharide compound including aldose-type glucose or aldose-type galactose is preferably amylose, cellulose, or agarose.

As used herein, the term "ion exchange resin" refers to a resin obtained by binding an ion exchanger to a polymer gas having a fine three-dimensional (3D) network structure, and is composed of a fixed ion bound to the polymer gas and a counter ion soluble in the solution having the opposite charge. Depending on the kind of exchanger, a cation exchange resin and an anion exchange resin are sorted, and may refer to a polymer acid and a polymer base, which are insoluble, respectively.

The kind of ion exchange resin includes an anion exchange resin and a cation exchange resin, and examples of the cation exchange resin may include strongly basic cation exchange resin Type 1, Type 2 (quaternary ammonium), and weakly basic anion exchange resin (primary to tertiary amine); and examples of the cation exchange resin may include strongly acidic cation exchange resin, and weakly acidic cation exchange resin.

The ion exchange resin is mainly configured such that an ion exchanger is introduced to a polymer gas having a fine 3D network structure, and is formed by copolymerization of a feed monomer (styrene) and a bifunctional or higher crosslinking agent (divinylbenzene: DVB), and DVB % is called the crosslinkability. The monomer is subjected to suspension polymerization using benzoyl peroxide as a catalyst in the presence of an insoluble medium (which is mainly water) by use of an organic suspension stabilizer such as PVA or an inorganic suspension stabilizer such as calcium carbonate, thus affording a copolymer in 20~50 mesh granular form.

The strongly acidic cation exchange resin is obtained by subjecting the above-prepared beads to sulfonation using concentrated sulfuric acid, chlorosulfonic acid, etc. The weakly acidic cation exchange resin mostly has a —COOH group and is synthesized by hydrolysis of a copolymer of acrylic acid ester, methacrylic acid ester, and DVB.

The strongly basic anion exchange resin Type 1 is prepared by subjecting copolymer beads of styrene and DVB to chloromethylation using chloromethylether in the presence of a Lewis acid catalyst such as $AlCl_3$, $SnCl_4$ or $ZnCl_2$ and then performing quaternization with a tertiary amine such as trimethylamine. Type 2 is obtained by subjecting copolymer beads to chloromethylation and then performing quaternization with dimethylethanolamine. The weakly basic anion exchange resin is obtained through amination of chloromethylated beads with primary and secondary amines. Also, it is prepared through amidation of a copolymer of DVB and acrylate with amine.

In the present invention, the anion exchange resin may include industrially useful polystyrene-based bead resin, and the terminal of the anion exchange resin is provided in the form of bicarbonate or aluminate to thus make a basic condition (pH 12~13) for isomerization.

Also, the cation exchange resin may include industrially useful polystyrene-based bead resin, and the terminal of the cation exchange resin is substituted with a proton using a 3N hydrochloric acid aqueous solution and thus pKa of the cation exchange resin where the proton is introduced at the terminal thereof is adjusted to about 1. Thereby, an acidic condition for dehydration is made.

In the reaction of step 1, the anion exchange resin is a polystyrene-based bead resin, as represented by [Chemical Formula 3] below, which has a quaternary ammonium or tertiary amine functional group at the terminal thereof and in which the counter ion is substituted with bicarbonate or aluminate to thus become weakly basic. To this end, the anion exchange resin has to be sufficiently washed with a sodium bicarbonate or sodium aluminate saturated solution before use.

[Chemical Formula 3]

Tertiary amine    Quatanary ammonium

● = Polystyrene bead
$R_1, R_2, R_3$ = H or Alkyl
$X^\ominus$ = $HCO_3^\ominus$ or $AlO_2^\ominus$

When glucose which is the aldose-type hexose compound is subjected to isomerization using the anion exchange resin having a structure represented by [Chemical Formula 3], it is converted into fructose which is a ketose-type hexose compound at a conversion efficiency of 30~50% and a selectivity of 70~90%.

The procedure of conversion of glucose which is the aldose-type hexose compound into fructose which is the ketose-type hexose compound by means of the anion exchange resin is regarded as carried out in such a manner that, under the basic condition around the anion exchange resin, while an electron in the aldehyde group at the terminal of aldose is delocalized to a carbon atom adjacent thereto, isomerization into ketose is conducted, as represented by [Chemical Formula 4] below.

[Chemical Formula 4]

Aldose

Ketose

Step 2 is converting the ketose-type hexose compound into a furan-based compound such as HMF or AMF through dehydration using the cation exchange resin.

In the reaction of step 2, it is preferred that the furan-based compound be 5-hydroxymethyl-2-furfural (HMF) or 5-alkoxymethyl-2-furfural (AMF), and that the alkoxy group of 5-alkoxymethyl-2-furfural (AMF) be a C1~C5 alkoxy group.

In the reaction of step 2, the cation exchange resin is a polystyrene-based bead resin, as represented by [Chemical Formula 5] below, which has a sulfonic acid functional group at the terminal thereof and in which the counter ion is substituted with a proton to thus become strongly acidic. To this end, the cation exchange resin has to be sufficiently washed using a hydrochloric acid aqueous solution or the like before use.

[Chemical Formula 5]

The procedure of conversion of the ketose-type hexose compound into the furan-based compound through dehydration using the cation exchange resin is represented by [Chemical Formula 6] below. As represented by [Chemical Formula 6], the ketose-type hexose compound converted from aldose is made into a furfural compound through removal of three water molecules together with a cyclization reaction under the acidic condition around the cation exchange resin (in this case, there is also an assertion that the dehydration reaction is carried out under the condition that the cyclization reaction does not take place—Acyclic intermediate mechanism).

[Chemical Formula 6]

-continued

In the present invention, the anion exchange resin, which functions to convert the aldose-type hexose compound into the ketose-type hexose compound through isomerization, and the cation exchange resin, which plays a role in converting the produced ketose-type hexose compound into the furan-based compound such as HMF or AMF through dehydration, may be used consecutively or simultaneously.

Taking into consideration the solubility of the hydrophilic hexose compound in the present invention, the organic solvent may be a polar solvent. Especially when using an aprotic polar solvent such as dioxane, THF (tetrahydrofuran), acetone, DMSO (Dimethyl sulfoxide), DMF (Dimethylformamide), NMP (N-methyl-2-pyrrolidone) or the like, HMF may be obtained as a final product. The use of a protic polar solvent such as ethanol, n-butanol or isopropanol may result in HMF and AMF as final products.

Moreover, when using an alcohol ($C_nH_{2n+1}OH$) solvent, the production yield of AMF is high, and preferably useful is ethanol, n-butanol, isopropanol or the like.

Also, the concentration of the hexose compound which is a starting material relative to the organic solvent upon reaction is 1~30% (wt/V) and preferably 10~20% (wt/V) in a mixed solution with the organic solvent. If the concentration of the hexose compound is less than 1%, productivity may decrease, and the cost for removing the organic solvent may increase. In contrast, if the concentration of the hexose compound exceeds 30%, reactivity may decrease.

Also, the anion exchange resin is used in an amount of 50~300 parts by weight, and preferably 100~200 parts by weight, based on 100 parts by weight of the aldose-type hexose compound. If the amount of the anion exchange resin is less than 50 parts by weight, the conversation rate may decrease. In contrast, if the amount thereof exceeds 300 parts by weight, the amount of byproducts may increase and profitability may decrease.

Also, the reaction temperature is set to 50~200° C., and preferably 70~150° C. If the reaction temperature is lower than 50° C., the reaction rate may decrease. In contrast, if the reaction temperature is higher than 200° C., the amount of byproducts may increase.

Mode for Invention

Below is a description of preferred embodiments of the present invention.

EXAMPLES

Examples 1 to 51

Step 1

In each of tubular type reactors, glucose was placed in an amount of 100 mg, and an anion exchange resin (Amberlite IRA-400, Amberlite IRA-900, Amberlite IRA-743, Amberlyst A-26) washed with a sodium bicarbonate ($NaHCO_3$) or sodium aluminate ($NaAlO_4$) saturated aqueous solution was placed in an amount of 50~300 mg (anion exchange resin/glucose (AER/Glu) weight ratio=0.5~3).

In each of the reactors, 3 mL of an organic solvent (DMSO, DMF, ethanol, dioxane, isopropanol) was placed, and the resulting mixture was stirred at 80~100° C. for a predetermined period of time. After termination of the reaction, each of the reactors were cooled to room temperature, diluted with HPLC (High Performance Liquid Chromatography) grade distilled water and analyzed with HPLC to measure fructose conversion yields. Samples were separated using an ion exclusion column (Bio-Rad Aminex HPX-87H 300×7.8 mm) by HPLC (Agilent 1200 series) and measured using an RID detector, thus determining the conversion yields.

The anion exchange resin, AER/Glu weight ratio, organic solvent, reaction time, reaction temperature and fructose yield in Examples 1 to 51 are shown in Table 1 below.

TABLE 1

| Ex. No. | Anion-Exchange Resin (AER) | AER/Glu (wt/wt) | Solvent | Time (min) | Temp (° C.) | Fructose Yield (%) |
|---|---|---|---|---|---|---|
| 1 | Amberlyst A-26 | 2 | DMSO | 30 | 100 | 28 |
| 2 | Amberlyst A-26 | 2 | DMSO | 30 | 100 | 38 |
| 3 | Amberlite IRA-400 | 2 | DMSO | 30 | 100 | 17 |
| 4 | Amberlite IRA-400 | 2 | DMSO | 30 | 100 | 1 |
| 5 | Amberlite IRA-900 | 2 | DMSO | 30 | 100 | 23 |
| 6 | Amberlite IRA-900 | 2 | DMSO | 30 | 100 | 5 |
| 7 | Amberlite IRA-743 | 2 | DMSO | 30 | 100 | 26 |
| 8 | Amberlite IRA-743 | 2 | DMSO | 30 | 100 | 20 |
| 9 | Amberlyst A-26 | 0.5 | DMSO | 10 | 100 | 6 |
| 10 | Amberlyst A-26 | 1 | DMSO | 10 | 100 | 18 |
| 11 | Amberlyst A-26 | 2 | DMSO | 10 | 100 | 25 |
| 12 | Amberlyst A-26 | 3 | DMSO | 10 | 100 | 25 |
| 13 | Amberlyst A-26 | 0.5 | DMSO | 30 | 100 | 12 |
| 14 | Amberlyst A-26 | 1 | DMSO | 30 | 100 | 23 |
| 15 | Amberlyst A-26 | 2 | DMSO | 30 | 100 | 34 |
| 16 | Amberlyst A-26 | 3 | DMSO | 30 | 100 | 30 |
| 17 | Amberlyst A-26 | 1 | DMSO | 10 | 100 | 18 |
| 18 | Amberlyst A-26 | 1 | DMSO | 30 | 100 | 17 |
| 19 | Amberlyst A-26 | 1 | DMSO | 60 | 100 | 21 |
| 20 | Amberlyst A-26 | 1 | DMSO | 120 | 100 | 19 |
| 21 | Amberlite IRA-743 | 1 | DMSO | 10 | 100 | 9 |
| 22 | Amberlite IRA-743 | 1 | DMSO | 30 | 100 | 24 |
| 23 | Amberlite IRA-743 | 1 | DMSO | 60 | 100 | 24 |
| 24 | Amberlite IRA-743 | 1 | DMSO | 120 | 100 | 31 |
| 25 | Amberlite IRA-900 | 2 | Water | 960 | 80 | 26 |
| 26 | Amberlite IRA-900 | 2 | DMSO | 960 | 80 | 15 |
| 27 | Amberlite IRA-900 | 2 | DMF | 960 | 80 | 37 |
| 28 | Amberlite IRA-900 | 2 | Ethanol | 960 | 80 | 45 |
| 29 | Amberlyst A-26 | 1 | Ethanol | 960 | 80 | 49 |
| 30 | Amberlite IRA-400 | 1 | Ethanol | 960 | 80 | 10 |

TABLE 1-continued

| Ex. No. | Anion-Exchange Resin (AER) | AER/Glu (wt/wt) | Solvent | Time (min) | Temp (°C.) | Fructose Yield (%) |
|---|---|---|---|---|---|---|
| 31 | Amberlite IRA-900 | 1 | Ethanol | 960 | 80 | 49 |
| 32 | Amberlite IRA-743 | 1 | Ethanol | 960 | 80 | 35 |
| 33 | Amberlite IRA-743 | 0.5 | DMSO | 10 | 100 | 7 |
| 34 | Amberlite IRA-743 | 1 | DMSO | 10 | 100 | 13 |
| 35 | Amberlite IRA-743 | 2 | DMSO | 10 | 100 | 18 |
| 36 | Amberlite IRA-743 | 3 | DMSO | 10 | 100 | 17 |
| 37 | Amberlite IRA-743 | 2 | DMSO | 60 | 100 | 21 |
| 38 | Amberlite IRA-743 | 2 | DMSO | 60 | 80 | 12 |
| 39 | Amberlite IRA-743 | 2 | DMF | 60 | 80 | 13 |
| 40 | Amberlite IRA-743 | 2 | Water | 60 | 80 | 26 |
| 41 | Amberlite IRA-743 | 2 | Ethanol | 60 | 80 | 37 |
| 42 | Amberlite IRA-743 | 2 | Ethanol | 120 | 80 | 49 |
| 43 | Amberlite IRA-743 | 2 | Ethanol | 180 | 80 | 57 |
| 44 | Amberlite IRA-743 | 2 | Dioxane | 180 | 80 | 53 |
| 45 | Amberlite IRA-743 | 2 | Isopropanol | 180 | 80 | 41 |
| 46 | Amberlite IRA-743 | 2 | Ethanol | 180 | 50 | 3 |
| 47 | Amberlite IRA-743 | 2 | Dioxane | 180 | 50 | 1 |
| 48 | Amberlite IRA-743 | 2 | Isopropanol | 180 | 50 | 1 |
| 49 | Amberlite IRA-743 | 2 | Ethanol | 240 | 80 | 59 |
| 50 | Amberlite IRA-743 | 2 | Ethanol | 300 | 80 | 60 |
| 51 | Amberlite IRA-743 | 2 | Ethanol | 360 | 80 | 61 |

*In Examples 2, 4, 6, 8 and 9 to 16, sodium aluminate (NaAlO$_4$) was used as an anion exchange resin washing solution, and in the other examples, sodium bicarbonate (NaHCO$_3$) was used.

Experimental Example 1

Comparison of Fructose Yields Depending on Anion Exchange Resin Washing Solution In Examples 1 to 8, each of the reactors after termination of the reaction was cooled to room temperature, diluted with HPLC grade distilled water and analyzed with HPLC to measure the yields. Samples were separated using an ion exclusion column (Bio-Rad Aminex HPX-87H 300×7.8 mm) by HPLC (Agilent 1200 series) and measured by means of an RID detector, thus determining the yields.

Figure 1:
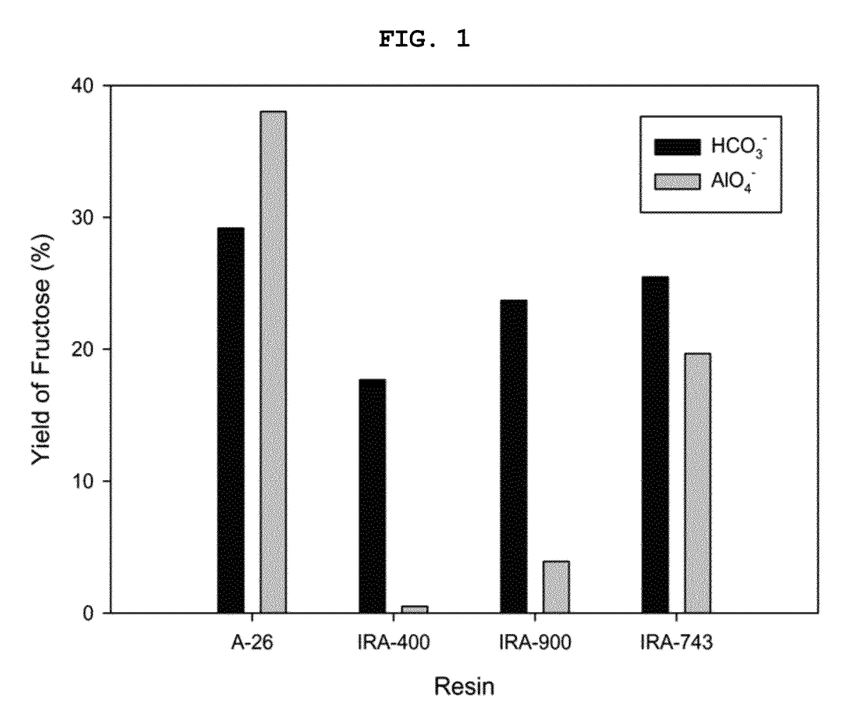
FIG. 1 illustrates comparison of the fructose yields depending on the anion exchange resin washing solution in Examples 1 to 8 according to the present invention.

The comparison results of the fructose yields depending on the anion exchange resin washing solution in Examples 1 to 8 are illustrated in FIG. 1.

As illustrated in FIG. 1, the anion exchange resin washed with sodium bicarbonate enables the production of fructose at a yield of 20~30% regardless of the kind thereof. On the other hand, in Example 2 using gel type Amberlite A-26 washed with sodium aluminate, fructose was produced at a high yield of 38%, but in Examples 3 to 6 using network type Amberlite IRA-400 and IRA-900, the isomerization effect into fructose was insignificant. Also, in Examples 6 and 7 using Amberlite IRA-743 having a tertiary amine functional group, the similar fructose conversion yields were obtained regardless of the kind of washing solution. This is because Amberlite IRA-743 is present in the form of free amine after washing with the basic solution, thus exhibiting no counter ion effects.

Experimental Example 2

Comparison of Fructose Yields Depending on Anion Exchange Resin/Glucose (AER/Glu) Weight Ratio After reaction in Examples 9 to 12 (reaction for 10 min, Amberlite A-26), Examples 13 to 16 (reaction for 30 min, Amberlite A-26), and Examples 33 to 36 (reaction for 10 min, Amberlite IRA-743), samples were taken, diluted with HPLC grade distilled water and analyzed with HPLC, thus measuring the yields.

As results of analysis, when the weight ratio of anion exchange resin relative to glucose was 2 (AER/Glu=2), the fructose yield was very high in Example 11 (25%), Example 15 (34%) and Example 35 (18%).

Figure 2:
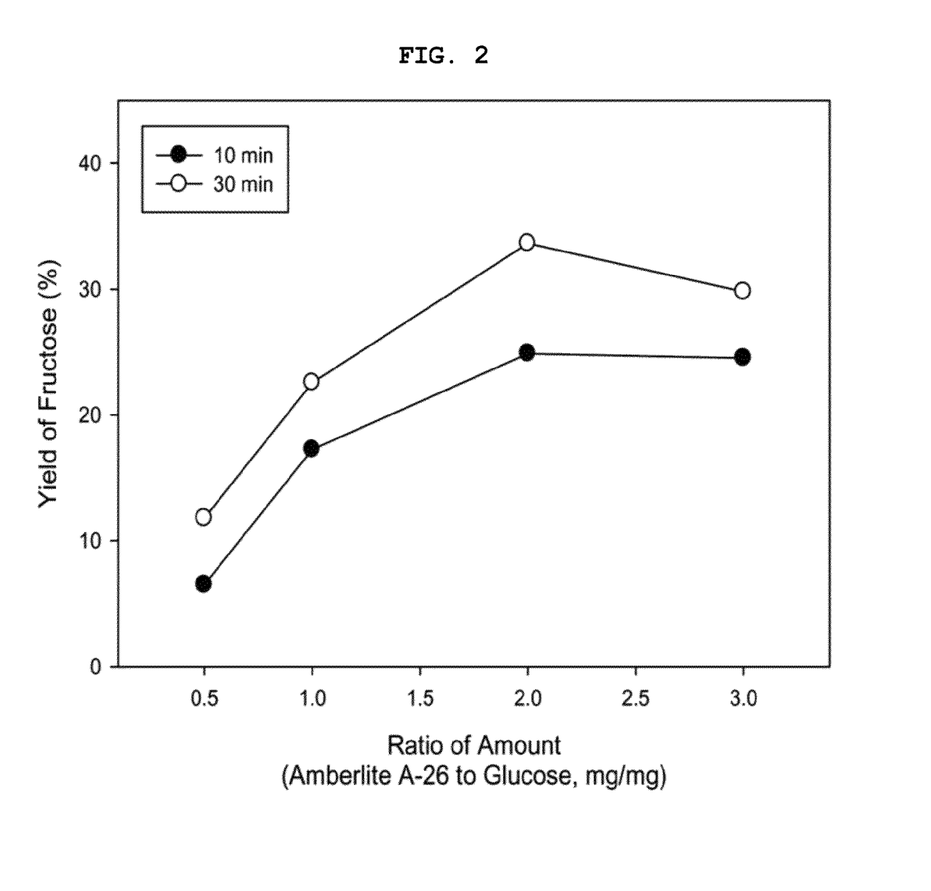
FIG. 2 illustrates comparison of the fructose yields depending on the anion exchange resin/glucose weight ratio in Examples 9 to 16 according to the present invention.

The fructose yields depending on the anion exchange resin/glucose weight ratio in Examples 9 to 16 are illustrated in FIG. 2. As illustrated in FIG. 2, the maximum conversion yield was exhibited at a weight ratio of 2 as above, and the reaction continued until 30 min had elapsed.

Experimental Example 3

Comparison of Fructose Yields Depending on Reaction Time with Anion Exchange Resin After reaction in Examples 17 to 20 (Amberlite A-26) and Examples 21 to 24 (Amberlite IRA-743), samples were taken, diluted with HPLC grade distilled water, and analyzed with HPLC, thus measuring the yields. The results of analysis are illustrated in FIG. 3.

Figure 3:
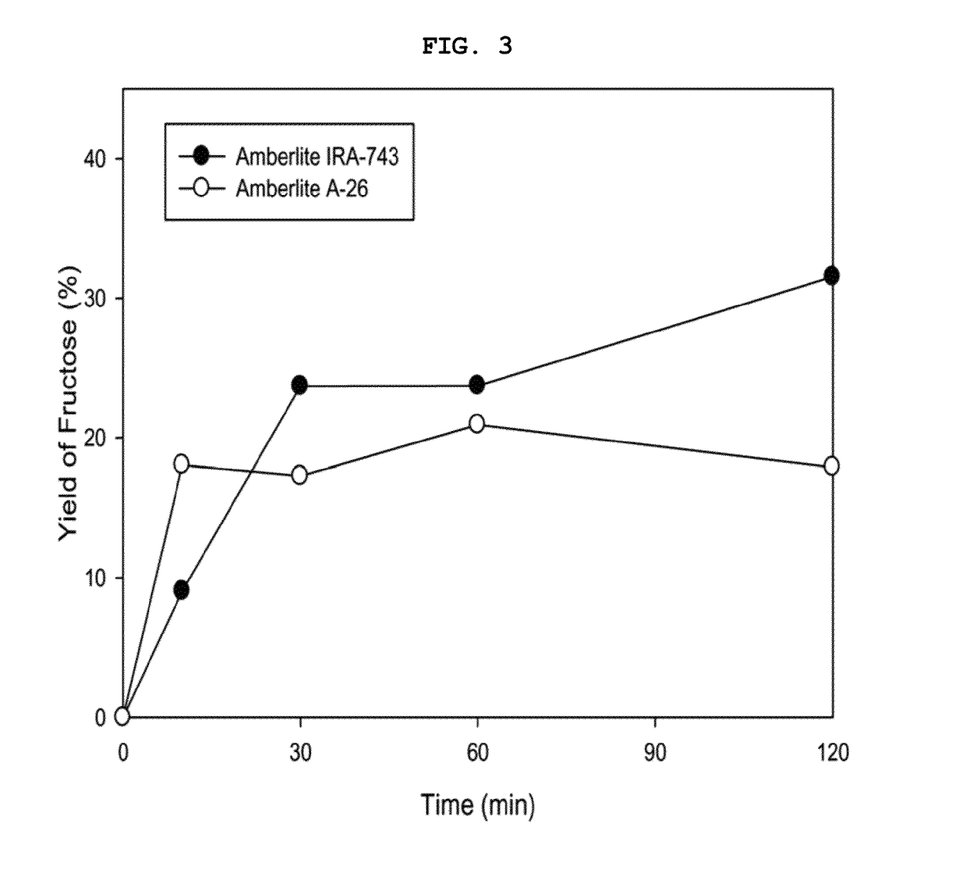
FIG. 3 illustrates comparison of the fructose yields depending on the reaction time in Examples 17 to 24 according to the present invention.

As illustrated in FIG. 3, when using Amberlite A-26, the maximum yield of about 20% was obtained in 10 min. Whereas, when Amberlite IRA-743 was used, 30 min or more was required to attain the maximum yield. However, the use of Amberlite IRA-743 was more significant in terms of the maximum yield.

When the reaction continued for 120 min or longer using Amberlite A-26, the fructose yield was 30% or more, and upon reaction for 16 hr in Example 29, the yield could be increased up to 49%, but brown byproducts were adsorbed on the resin.

Experimental Example 4

Comparison of Fructose Yields Depending on Reaction Organic Solvent

After reaction in Examples 25 to 28, samples were taken and analyzed with HPLC, and the conversion efficiency of glucose and the selectivity and yield of fructose depending on the reaction organic solvent were analyzed. The results are illustrated in FIG. 4.

Figure 4:
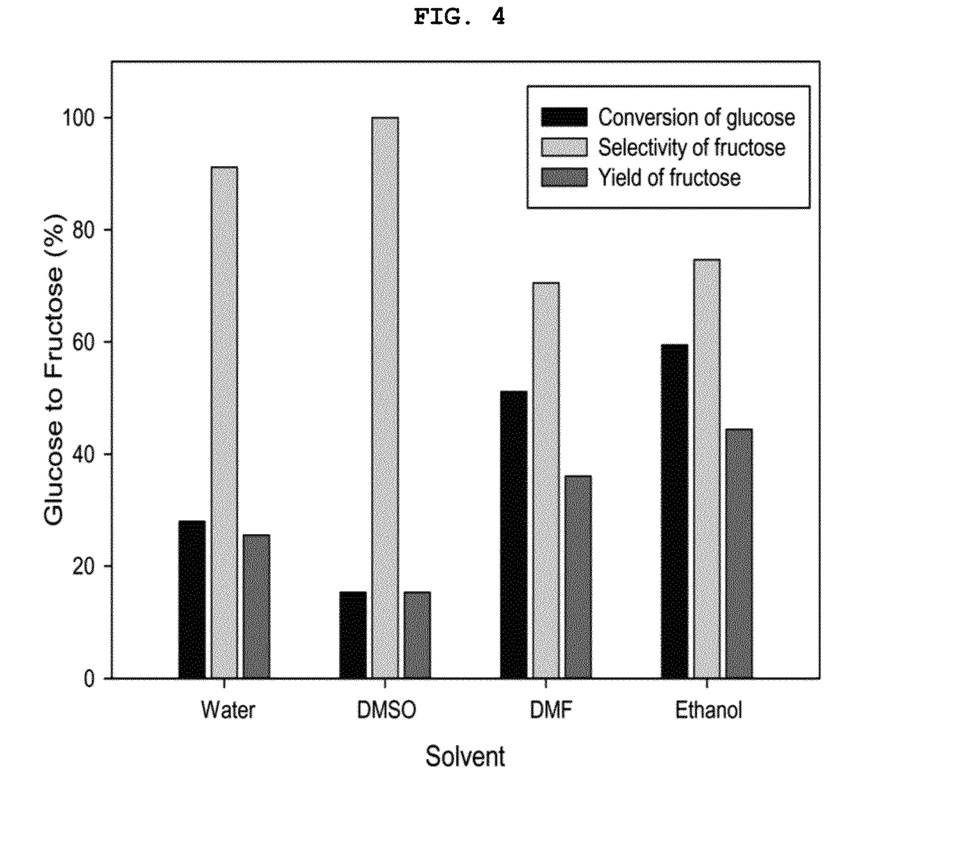
FIG. 4 illustrates comparison of the fructose yields depending on the reaction organic solvent in Examples 25 to 28 according to the present invention.

As illustrated in FIG. 4, when using water and DMSO as reaction organic solvents together with Amberlite IRA-900, the selectivity of fructose was as high as 90% or more, but the conversion efficiencies of glucose were as poor as 26% and 15% respectively even after 16 hr. However, when using ethanol as the protic polar solvent, fructose could be obtained at a high yield of 45% or more despite low solubility of glucose.

When ethanol (b.p. 78° C.) is used as the reaction organic solvent in this way, it is more easily removed because of a boiling point lower than DMSO (b.p. 189° C.) or DMF (b.p. 153° C.), and enables EMF (5-ethoxymethyl-2-furfural) known as a next-generation biofuel to be directly obtained.

As well, in Examples 44 and 45 where the reaction was carried out at 80° C. under the condition that the weight ratio of Amberlite IRA-743 anion exchange resin relative to glucose was 2 in the presence of dioxane and isopropanol as the polar solvents other than ethanol, the fructose yields reached 53% and 41% respectively in 3 hr, which were evaluated to be relatively good.

On the other hand, in Examples 46 to 48 where the reaction temperature was decreased to 50° C., the fructose yield was very low to the extent of 1~3% regardless of the kind of organic solvent.

Experimental Example 5

Comparison of Fructose Yields Depending on Anion Exchange Resin

After reaction in Examples 29 to 32, samples were taken and analyzed with HPLC, and the conversion efficiency of glucose, the selectivity of fructose and the fructose yield were analyzed. The results are illustrated in FIG. 5.

Figure 5:
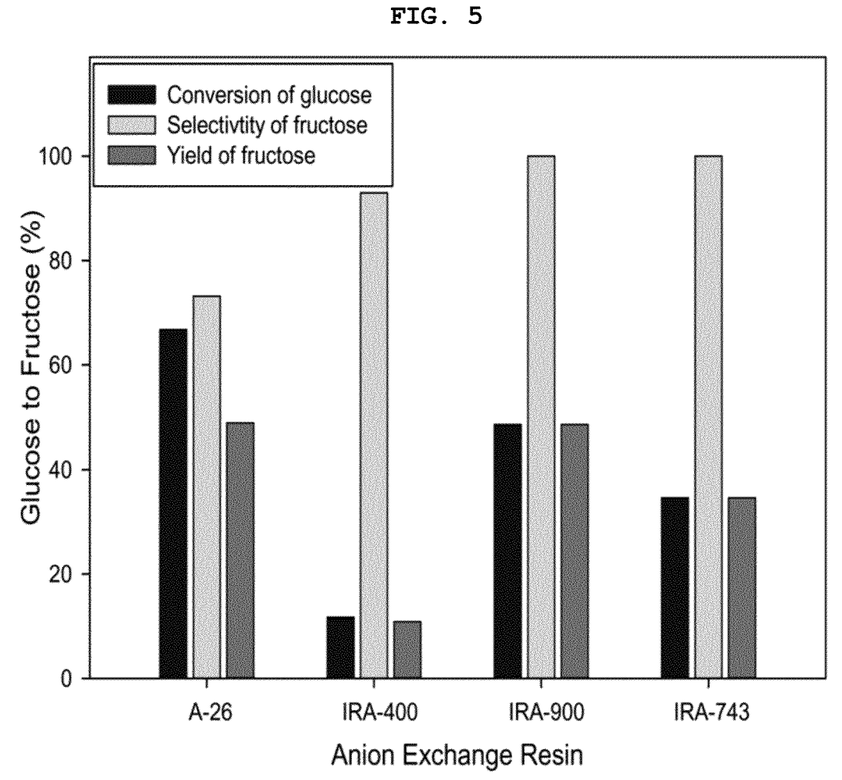
FIG. 5 illustrates comparison of the fructose yields depending on the kind of anion exchange resin in Examples 29 to 32 according to the present invention.

As illustrated in FIG. 5, in Example 29 using Amberlite A-26 as the anion exchange resin and Example 31 using Amberlite IRA-900, fructose was produced at a high yield of 49%. In Example 29 using Amberlite A-26, the conversion efficiency of glucose was as high as 67%, but the selectivity of fructose was as low as 73%. Whereas, in Example 31 using Amberlite IRA-900, the conversion efficiency of glucose was 49% which was lower than when using Amberlite A-26, but the selectivity of fructose approximated to 100%.

Meanwhile, after reaction in Examples 1, 3, 5 and 7, samples were taken and analyzed with HPLC, thus measuring fructose yields. As such, as is apparent from Table 1, the fructose yields of Example 1 using Amberlyst A-26 and Example 7 using Amberlite IRA-743 were the highest to the extent of 28% and 26%. In Example 1, however, the fructose yield was high but byproducts were generated together.

Particularly in Example 43 using Amberlite IRA-743, when the reaction was carried out at 80° C. using ethanol under the condition that the weight ratio of the anion exchange resin relative to glucose was 2, the fructose conversion yield reached 57% in 3 hr.

Examples 52 to 56

Consecutive Steps 1 and 2

In a tubular type reactor, glucose and an anion exchange resin Amberlite IRA-743 were placed and then reacted for a predetermined period of time (step 1), and consecutively, a cation exchange resin Amberlyst 15 was added and then reaction was carried out under predetermined temperature and time conditions (step 2). As such, the ion exchange resin used in the previous step was removed through filtration, and then the new ion exchange resin was added, and anion/cation exchange resins were alternately used.

The detailed reaction conditions in Examples 52 to 56 are shown in Table 2 below.

TABLE 2

| Ex. No. | Glucose (mg) | AER (mg) | CER (mg) | Solvent | Treatment Time (h) | Temp (° C.) | Conversion (%) | HMF Yield (%) | AMF Yield (%) |
|---|---|---|---|---|---|---|---|---|---|
| 52 | 100 | 100 | 100 | DMSO | 3 + 2 | 100 | 24 | 16 | — |
| 53 | 100 | 200 | 100 | DMSO | (1 + 1) × 3 | 100 | 52 | 29 | — |
| 54 | 100 | 200 | 100 | DMSO | (0.5 + 0.5) × 6 | 100 | 76 | 26 | — |
| 55 | 100 | 200 | 100 | DMF | (1 + 1) × 3 | 100 | 43 | 34 | — |
| 56 | 100 | 200 | 100 | Ethanol | (1 + 1) × 3 | 80 + 100 | 77 | 11 | 23 |

*Treatment Time: (a + b) × c, wherein a is the reaction time of step 1, b is the reaction time of step 2, and c is the number of repetition operations.
*In Example 56, the reaction temperature '80 + 100' means 80° C. in step 1 and 100° C. in step 2, and AMF is EMF (5-ethoxymethyl-2-furfural).

Examples 57 to 62

Simultaneous Steps 1 and 2

In a tubular type reactor, glucose, an anion exchange resin Amberlite IRA-743 washed with a sodium bicarbonate saturated solution, and a cation exchange resin Amberlylst 15 were simultaneously placed, and reacted under predetermined temperature and time conditions in the presence of an organic solvent (DMSO, DMF, ethanol, n-butanol).

The detailed reaction conditions in Examples 57 to 62 are shown in Table 3 below.

TABLE 3

| Ex. No. | Glucose (mg) | AER (mg) | CER (mg) | Solvent | Treatment Time (h) | Temp (° C.) | Conversion (%) | HMF Yield (%) | AMF Yield (%) |
|---|---|---|---|---|---|---|---|---|---|
| 57 | 100 | 100 | 100 | DMSO | 5 | 100 | 28 | 7 | — |
| 58 | 100 | 100 | 100 | DMF | 5 | 100 | 65 | 13 | — |

TABLE 3-continued

| Ex. No. | Glucose (mg) | AER (mg) | CER (mg) | Solvent | Treatment Time (h) | Temp (°C.) | Conversion (%) | HMF Yield (%) | AMF Yield (%) |
|---|---|---|---|---|---|---|---|---|---|
| 59 | 100 | 200 | 100 | DMF | 5 | 100 | 63 | 23 | — |
| 60 | 100 | 200 | 100 | DMF | 9 | 100 | 70 | 23 | — |
| 61 | 100 | 200 | 200 | Ethanol | 4 | 100 | — | — | 25 |
| 62 | 100 | 200 | 200 | n-butanol | 4 | 120 | — | — | 25 |

*Treatment Time: (a + b) × c, wherein a is the reaction time of step 1, b is the reaction time of step 2, and c is the number of repetition operations.
*In Example 61, AMF is EMF (5-ethoxymethyl-2-furfural), and in Example 62, AMF is BMF (5-butoxymethyl-2-furfural).
*Yields of Examples 61 and 62 were measured by weight after separation of only AMF (EMF, BMF) using the column.

Comparative Example 1

Use of No Anion Exchange Resin

In a tubular type reactor, 100 mg of glucose and 100 mg of Amberlyst 15 as a proton-substituted cation exchange resin were placed, added with 3 mL of an organic solvent DMSO, and then stirred at 100° C. for 5 hr in the absence of an anion exchange resin. As results of HPLC analysis after termination of the reaction, HMF which is the furan-based compound was not produced under the above reaction conditions.

Experimental Example 6

Analysis of Changes in Product Yield Over Time Upon Conversion of Glucose into HMF and EMF In Example 56, glucose was added, and Amberlite IRA-743 as the anion exchange resin and Amberlyst 15 as the cation exchange resin were alternately used at 80° C. and 100° C. for 1 hr each in the presence of an ethanol organic solvent, and thus changes in products over time were analyzed. The results are illustrated in FIG. 6.

Figure 6:
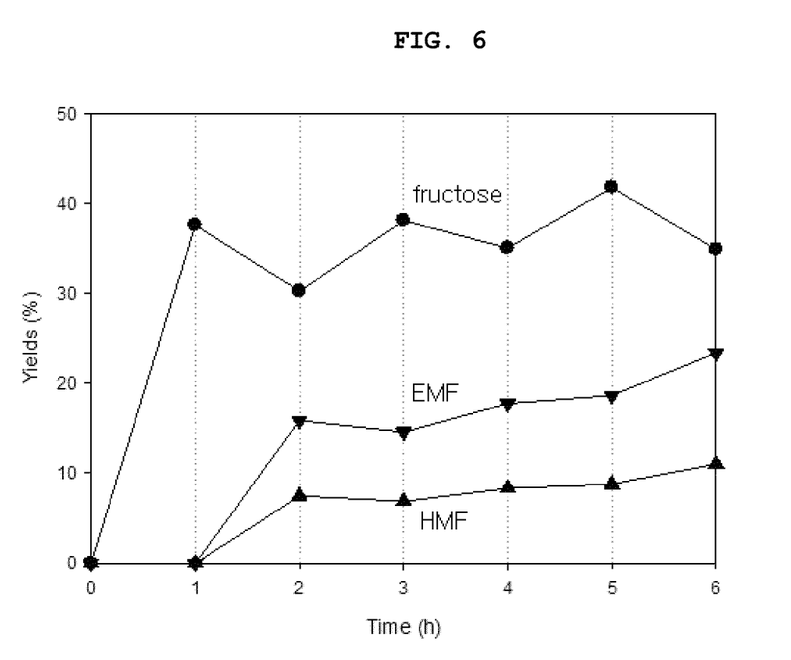
FIG. 6 illustrates changes in product yield over time in a conversion reaction into HMF and EMF in Example 56 according to the present invention.

As illustrated in FIG. 6, isomerization of glucose into fructose was carried out when using the anion exchange resin, thus increasing the fructose production yield. When using the cation exchange resin, the production of fructose was decreased, and HMF and EMF were produced.

As shown in Experimental Examples 1 to 6, the method of producing the furan-based compound such as HMF or AMF according to the present invention is advantageous because not only a ketose-type hexose compound which may be obtained only from limited supply sources including food resources, but also an aldose-type hexose compound very abundant in nature, may be converted into a furan-based compound such as HMF or AMF. Also, compared to the conventional method using an ionic liquid and a metal catalyst developed to convert the aldose-type hexose compound into the furan-based compound, the method of the present invention obviates the need for expensive reagents and thus may reduce the production costs when taking into consideration industrial mass production.

Compared to the conventional method of converting a hexose compound into a furan-based compound using a biphasic system, the selection of the organic solvent is not limited in the present invention, and a heterogeneous catalyst may be used, thus facilitating separation and purification. Furthermore, the use of a protic polar solvent makes it possible to directly produce chemically stable AMF which is usable as a biofuel having high energy density, as well as HMF.

Briefly, when compared to conventional methods using only the cation exchange resin, the method of the present invention may promote conversion into the ketose-type hexose compound through isomerization by the anion exchange resin, thus obtaining high conversion efficiency of the aldose-type hexose compound, and the hexose compound may be used at as high a concentration as at least 10-fold.

Although the preferred embodiments of the present invention have been disclosed for illustrative purposes, those skilled in the art will appreciate that various modifications, additions and substitutions are possible, without departing from the scope and spirit of the invention as disclosed in the accompanying claims.

INDUSTRIAL APPLICABILITY

In a production method according to the present invention, anion/cation exchange resins are simultaneously or consecutively used as catalysts, and thereby an aldose-type hexose compound obtained from biomass can be made into 5-hydroxymethyl-2-furfural (HMF) or its alkyl ether derivative, that is, 5-alkoxymethyl-2-furfural (AMF), without the use of expensive reagents.

Also, the selection of an organic solvent is not limited, and the use of a heterogeneous catalyst is possible, thus facilitating separation and purification and directly producing chemically stable AMF. Furthermore, the conversion efficiency of the aldose-type hexose compound is high, and the hexose compound can be used at as high a concentration as at least 10-fold.

The invention claimed is:

1. A method of producing a furan-based compound, comprising reacting an aldose-type hexose compound in the presence of an anion exchange resin and a cation exchange resin in the presence of an organic solvent.

2. The method of claim 1, comprising:
   (i) isomerizing the aldose-type hexose compound with the anion exchange resin to give a ketose-type hexose compound; and
   (ii) dehydrating the ketose-type hexose compound with the cation exchange resin to give the furan-based compound.

3. The method of claim 2, wherein steps (i) and (ii) are conducted simultaneously or consecutively.

4. The method of claim 1, wherein the aldose-type hexose compound is aldose-type glucose; aldose-type galactose; or a saccharide compound including aldose-type glucose or aldose-type galactose.

5. The method of claim 4, wherein the saccharide compound including aldose-type glucose or aldose-type galactose is amylose, cellulose or agarose.

6. The method of claim 1, wherein the furan-based compound is 5-hydroxymethyl-2-furfural (HMF) or 5-alkoxymethyl-2-furfural (AMF).

7. The method of claim 6, wherein an alkoxy group of 5-alkoxymethyl-2-furfural (AMF) is a C1~C5 alkoxy group.

8. The method of claim 1, wherein the anion exchange resin is a basic anion exchange resin as a polystyrene-based bead resin, which has a quaternary ammonium or tertiary amine functional group at a terminal thereof and in which a central ion is substituted with bicarbonate or aluminate and thus pH around the exchange resin falls in a range of 12~13.

9. The method of claim 1, wherein the cation exchange resin is an acidic cation exchange resin as a polystyrene-based bead resin, which has a sulfonic acid functional group at a terminal thereof and in which a central ion is substituted with a proton and thus pKa is 1~2.

10. The method of claim 1, wherein the organic solvent is an aprotic polar solvent.

11. The method of claim 10, wherein the aprotic polar solvent is any one selected from among dioxane, tetrahydrofuran (THF), acetone, dimethyl sulfoxide (DMSO), dimethylformamide (DMF) and 1-methyl-2-pyrrolidone (NMP).

12. The method of claim 1, wherein the organic solvent is a protic polar solvent.

13. The method of claim 12, wherein the protic polar solvent is an alcohol solvent.

14. The method of claim 12, wherein the protic polar solvent is any one selected from among ethanol, n-butanol and isopropanol.

15. The method of claim 1, wherein the aldose-type hexose compound has a concentration of 1~30% (wt/V) in a mixed solution with the organic solvent.

16. The method of claim 1, wherein the anion exchange resin is used in an amount of 50~300 parts by weight based on 100 parts by weight of the aldose-type hexose compound.

17. The method of claim 1, wherein producing the furan-based compound is performed at a reaction temperature of 50~200° C.

* * * * *